United States Patent [19]

Wilk

[11] Patent Number: 5,271,383
[45] Date of Patent: Dec. 21, 1993

[54] METHOD FOR REDUCING INTUSSUSCEPTION

[76] Inventor: Peter J. Wilk, 185 W. End Ave., New York, N.Y. 10023

[21] Appl. No.: 894,082

[22] Filed: Jun. 5, 1992

[51] Int. Cl.$^5$ .................. A61B 1/06; A61M 31/00; A61M 29/00
[52] U.S. Cl. .................. 128/6; 604/49; 604/96; 604/98
[58] Field of Search .................. 128/4, 6-10; 604/96-98, 104, 109, 54, 49; 606/191, 197

[56] References Cited

U.S. PATENT DOCUMENTS

| | | | |
|---|---|---|---|
| 4,441,495 | 4/1984 | Hicswa | |
| 4,893,634 | 1/1990 | Kulik et al. | 604/54 X |
| 4,957,486 | 9/1990 | Davis | 604/96 |
| 5,029,574 | 7/1991 | Shimamura et al. | 128/6 |

FOREIGN PATENT DOCUMENTS 9101687 2/1991 PCT Int'l Appl. .

Primary Examiner—Richard J. Apley
Assistant Examiner—John P. Leubecker
Attorney, Agent, or Firm—R. Neil Sudol; Henry D. Coleman

[57] ABSTRACT

A method for reducing intussusception comprises the steps of (a) introducing into a colon a flexible insertion member of an endoscope, (b) moving the insertion member through the colon, (c) using optical components of the endoscope to view contents and surfaces of the colon during the step of moving, (d) upon visualization of a small intestine section folded back into the colon, inflating a balloon at a distal end of the insertion member, the balloon being transparent to optical radiation, (e) pushing the inflated balloon against the intussuscepted small intestine section to force the small intestine section out of the colon, and (f) optically monitoring, via the optical components and through the balloon, the intussuscepted small intestine section and the colon during the step of pushing.

9 Claims, 4 Drawing Sheets

5,271,383

METHOD FOR REDUCING INTUSSUSCEPTION

BACKGROUND OF THE INVENTION

This invention relates to a method or procedure for reducing intestinal intussusception. This invention also relates to a device for use in such a method.

Intussusception is that condition of a person's digestive tract wherein a section of the small intestine is folded back into the colon. This condition can be lethal. In such cases, there is a loss of blood supply to the folded-back or intussuscepted section of the small intestine. Gangrene eventually occurs.

Traditional treatment of intussusception begins with a barium enema. If the pressure of the barium fluid is insufficient to rectify the condition, open abdominal surgery must be performed. Such surgery, of course, is costly and traumatic to the patient. The surgery is time consuming and requires a lengthy hospital stay.

OBJECTS OF THE INVENTION

An object of the present invention is to provide a method or procedure for reducing intestinal intussusception.

A related object of the invention is to provide a device utilizable in performing the procedure.

Another object of the present invention is to provide such a method or procedure which does not require open abdominal surgery.

Another, associated, object of the present invention is to provide such a procedure which reduces hospital stay and tauma to the patient.

A further particular object of the present invention is to provide such a procedure which is potentially less costly than open abdominal surgery.

Other objects of the present invention will be apparent from the detailed descriptions and drawings included herein.

SUMMARY OF THE INVENTION

A method for reducing intussusception comprises, in accordance with the present invention, the steps of (a) introducing into a colon a flexible insertion member of an endoscope, (b) moving the insertion member through the colon, (c) using optical components of the endoscope to view contents and surfaces of the colon during the step of moving, (d) upon visualization of a small intestine section folded back into the colon, inflating a balloon at a distal end of the insertion member, the balloon being transparent to optical radiation, (e) pushing the inflated balloon against the intussuscepted small intestine section to force the small intestine section out of the colon, and (f) optically monitoring, via the optical components and through the balloon, the intussuscepted small intestine section and the colon during the step of pushing.

Pursuant to one alternative feature of the present invention, the balloon is attached to an outer surface of the insertion member. In that event the step of inflating may include the step of forcing a fluid under pressure through an auxiliary channel provided along an outer surface of the insertion member. Alternatively, if the balloon communicates with a biopsy channel in the endoscope insertion member, for example, where the balloon is attached around the circumference of the insertion member at the distal end thereof, the inflation of the balloon may be accomplished by forcing a fluid under pressure through the biopsy channel According to another feature of the present invention, the pushing of the balloon may entail the step of shifting the insertion member of the endoscope further in a distal direction through the colon.

According to a further feature of the present invention, the procedure includes the additional steps of attaching the balloon in a collapsed configuration to the outer surface of the insertion member prior to the step of introducing the insertion member into the colon and removing the balloon from the outer surface of the insertion member subsequently to a withdrawal of the insertion member from the colon after pushing of the intussuscepted small intestine section out of the colon.

Pursuant to a specific embodiment of the present invention, the balloon is attached to a distal end of a flexible tube disposed at least partially in a biopsy channel in the insertion member. The balloon is disposed in a collapsed configuration inside a distal end portion of the biopsy channel prior to the inflating of the balloon. Accordingly, the procedure includes the further step of shifting the tube through the biopsy channel to eject the balloon from the distal end portion of the biopsy channel upon visualization of the intussuscepted small intestine section and prior to the inflation of the balloon.

Pursuant to another feature of the present invention, the balloon is deflated upon the removal of the small intestine section from the colon. The endoscope insertion member is then withdrawn from the colon. In a supplemental step, the deflated balloon is retracted back into the distal end portion of the biospy channel prior to the withdrawal of the endoscope insertion member from the colon.

Where the balloon is attached to the distal end of a tube in the endoscope biopsy channel, the pushing of the small intestine section may be implemented in part or entirely by shifting the tube further in a distal direction through the biopsy channel.

An endoscopic device for use in the method of the present invention comprises an endoscope insertion member having a biospy channel, a tubular member slidably inserted into the biopsy channel, and a balloon attached to a distal end of the tubular member. The tubular member has a longitudinally extending duct which which the balloon communicates and the balloon is made of a material transparent to optical radiation. An inflation device is coupled to the tubular member for forcing a fluid under pressure through the duct to expand the balloon from a collapsed configuration to an expanded configuration.

Another endoscopic device for use in the method of the present invention comprises an endoscope insertion member having an outer surface, a balloon made of a material transparent to optical radiation, a fastening agent removably attaching the balloon to the outer surface on one side of the insertion member at a distal end thereof, and an inflation device for expanding the balloon from a collapsed configuration to an expanded configuration. The inflation device includes a tube or duct coupled to the balloon and extending in part in a longitudinal direction along the outer surface from the distal end to a proximal end of the insertion member.

A method or procedure in accordance with the present invention for reducing intussusception does not require open abdominal surgery. Accordingly, hospital stay and tauma to the patient are reduced. Owing in part to the reduced hospital stay, a procedure in accordance with the present invention is potentially less costly than open abdominal surgery.

DETAILED DESCRIPTION

Figure 1:
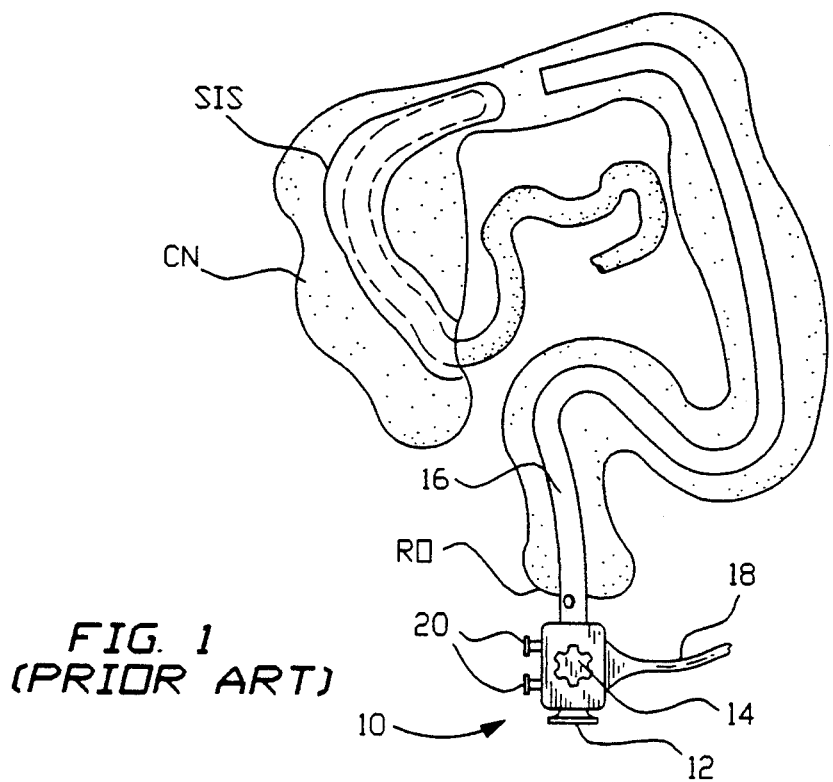
FIG. 1 is a schematic cross-sectional view, on a substantially reduced scale, of an endoscope inserted into a colon with an intussusscepted intestine.

As illustrated in FIG. 1, in an intestinal intussussception, a small intestine section SIS is folded back onto itself in a telescoping fashion inside an associated colon CN. An endoscope or colonoscope 10 may be inserted through colon CN from a rectal orifice RO to the intussuscepted intestinal section SIS to view the condition in accordance with conventional techniques. Endoscope 10 illustrated in FIG. 1 is a conventional instrument with an eyepiece 12 for viewing internal organic features of a patient, knobs 14 for turning the distal tip of an endoscope insertion member 16, a power line 18, and various controls 20 for the application of water and suction.

Figure 2A:
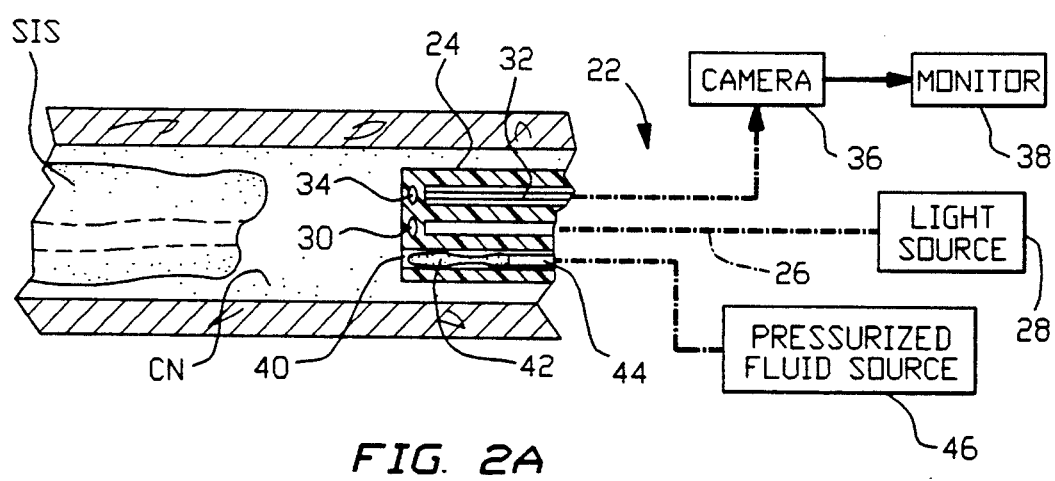
FIG. 2A is partially a schematic cross-sectional view, on a larger scale, and partially a block diagram of an endoscope in accordance with the present invention inside a colon with an intussusception, showing an initial stage in a procedure in accordance with the present invention.

FIG. 2A shows an endoscopic device or assembly 22 specifically designed for intussusception reduction. A flexible insertion member 24 incorporates an optical fiber 26 for carrying radiant energy from a light source 28 to a lens 30 at the distal tip of insertion member 24. A fiber optic bundle 32 extends from a focusing lens 34 at the distal tip of insertion member 24 to a camera or charge coupled device 36. Camera 36 is in turn connected to a video monitor 38 for displaying an image of internal organic structures of a patient.

Insertion member 24 is further provided with a conventional biopsy channel 40 in which a tubular member 44 is slidably inserted. Tubular member 44 carries an inflatable balloon 42 at its distal end. Balloon 42 is made of optically transparent flexible material, whereby the optical components 32, 34, 36, 38 of the endoscopic assembly 22 may be used upon an inflation of balloon 42, as described hereinafter.

At a proximal end, tubular member 44 is connected to a source 46 of pressurized or pressurizable fluid. The fluid is preferably an optically transparent saline solution appropriate for intravenous feeding. Fluid source 46 may take the form of a syringe or a pump with a pressure valve (not shown).

At the start of an intussusception reduction procedure, balloon 42 is disposed in a collapsed configuration in a distal end portion of biopsy channel 40, as illustrated in FIG. 2A. Endoscope insertion member 24 is introduced into and moved through colon CN. Optical components 32, 34, 36, 38 are used to to view contents and surfaces of the colon during the endoscope insertion operation.

Figure 2B:
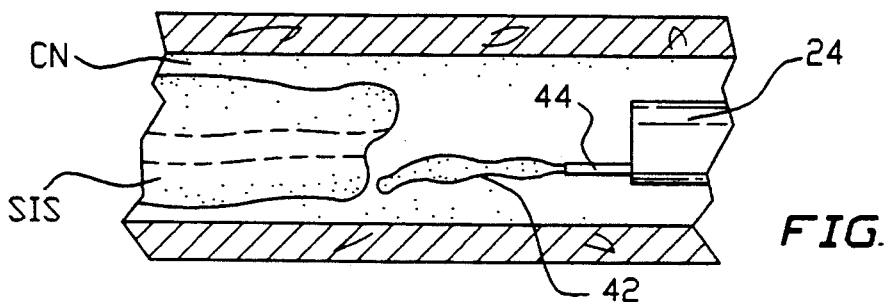
FIGS. 2B-2D are partially cross-sectional and partially side elevational views of the endoscope of FIG. 2A inside the colon with the intussusception, showing successive subsequent steps in a procedure in accordance with the present invention.
Figure 2C:
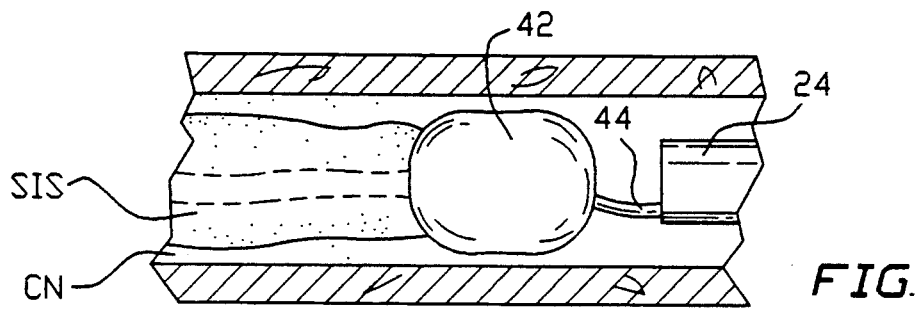
Figure 2D:
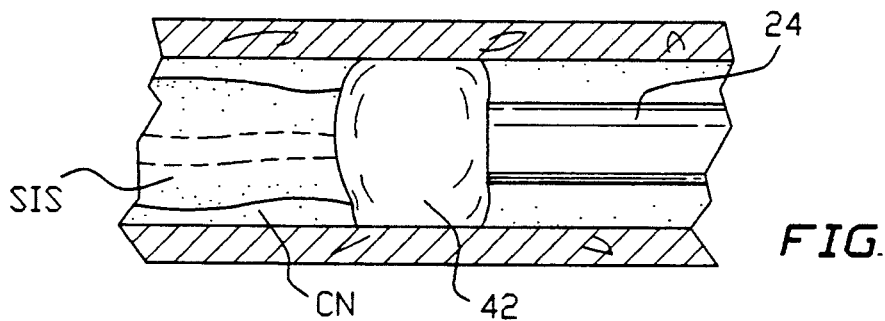

Upon a visual detection of intestinal section SIS via monitor 38, tubular member 44 is shifted in the distal direction through biospy channel 40, thereby ejecting balloon 42 from the distal end portion of the channel, as shown in FIG. 2B. Balloon is then inflated by fluid from source 46, the fluid being forced through a duct (not shown) in tubular member 44. The inflated balloon 42, illustrated in FIG. 2C, is brought into engagement with intestinal section SIS and pushed against the intestinal section to force it back out of colon CN. The pushing of balloon 42 may be accomplished to some extent by shifting tubular member 44 further in the distal direction through biospy channel 40. As depicted in FIG. 2D, additional pressure is exerted on balloon 42 by bringing the distal end of endoscope insertion member 24 into contact with balloon 42. To that end, tubular member 44 is withdrawn back into channel 40.

The progress of the intussusception reduction procedure is optically monitored, via optical components 32, 34, 26, 38 and through balloon 42. This enables the procedure to be interrupted, if neccessary, for readjusting the position of balloon 42 relative to intestinal section SIS, for example.

Upon the completion of the intussusception reduction procedure, i.e., upon the pushing of intestinal section SIS back out of colon CN, balloon 42 is deflated and endoscope insertion member 24 withdrawn from colon CN. Optionally, balloon 42 is retracted back into the distal end portion of channel 40 prior to the completed withdrawal of endoscope insertion member 24 from colon CN.

Figure 3A:
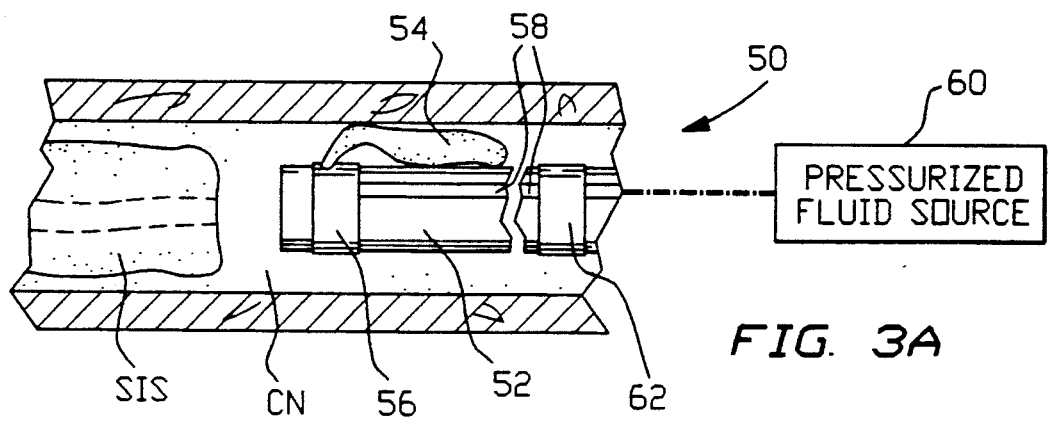
FIGS. 3A-3C are partially cross-sectional and partially side elevational views showing use of another endoscope in an intussusception reduction procedure in accordance with the present invention.
Figure 3B:
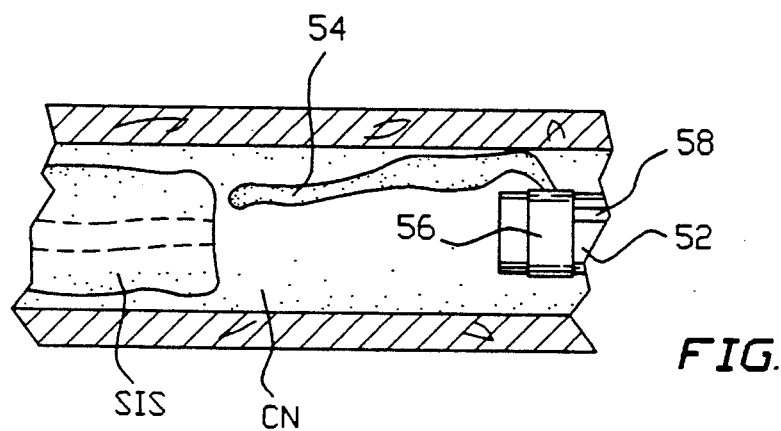
Figure 3C:
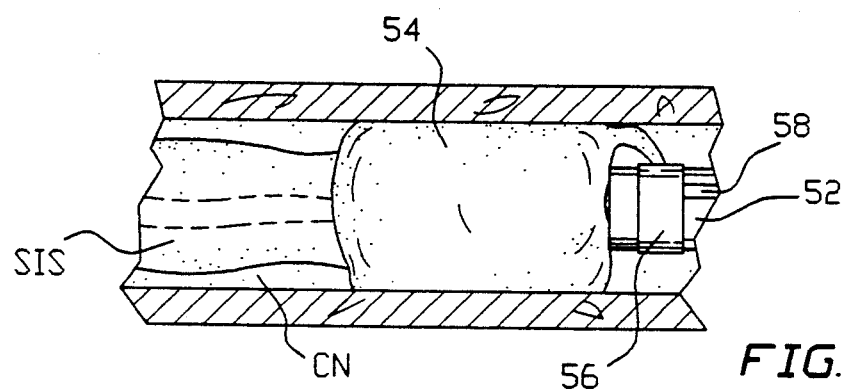

FIGS. 3A-3C illustrate an alternative endoscopic assembly 50 for use in an intussusception reduction procedure. An endoscope insertion member 52 is provided with all the optical components of a conventional colonoscope (see, for instance, FIG. 2A). The optical components have not been illustrated in FIGS. 3A-3C for purposes of simplicity. A transparent inflatable balloon 54 is attached via a sleeve or collar 56 to an outer surface of insertion member 52 along one side thereof. A tube or duct 58 communicating with balloon 54 extends therefrom in a proximal direction along insertion member 52 to a pressurized or pressurizable fluid source 60. Tube or duct 58 may be secured to insertion member 52 by a plurality of tape strips or collars 62 spaced from one another along the length of insertion member 52.

Alternatively, the tube or ductr 58 may be an integral part of a removable sheath (not shown) extending the length of insertion member 52.

As illustrated in FIG. 3A, balloon 54 drags alongside the distal end of insertion member 52 during an endoscope insertion operation. Upon the visualization of intussuscepted intestinal section SIS, endoscope insertion member 52 may be partially withdrawn to bring balloon 54 in front of the distal end of insertion member 52, as depicted in FIG. 3B. Balloon 54 is then inflated via fluid from source 60 and pressed against intestinal section SIS, as shown in FIG. 3C.

Balloon 54 is attached to the distal end of endoscope insertion member 52 prior to an introduction thereof into colon CN. Subsequently, collars or tapes 56 and 62 are removed to enable the disassembly of balloon 54 and tube 58 from insertion member 52.

Collars or tapes 52 and 62 may be adhesively joined to the outer surface of endoscope insertion member 52. However, other equivalent attachment elements may alternatively or additionally be utilized.

Figure 4A:
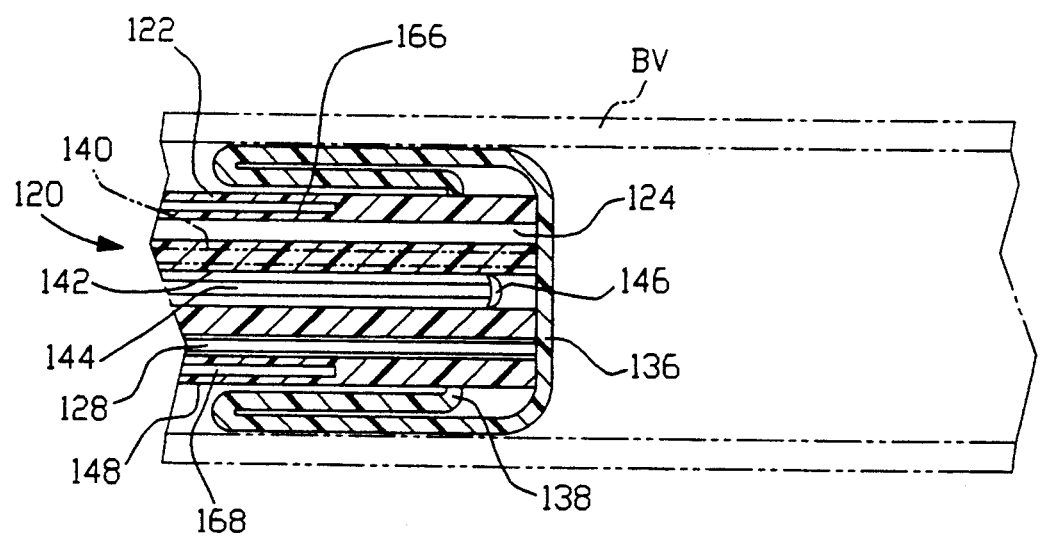
FIGS. 4A-4C are schematic partial cross-sectional views of a prior art endoscopic device which may be utilized in a method in accordance with the present invention, showing successive steps in the utilization of the endoscopic device.
Figure 4B:
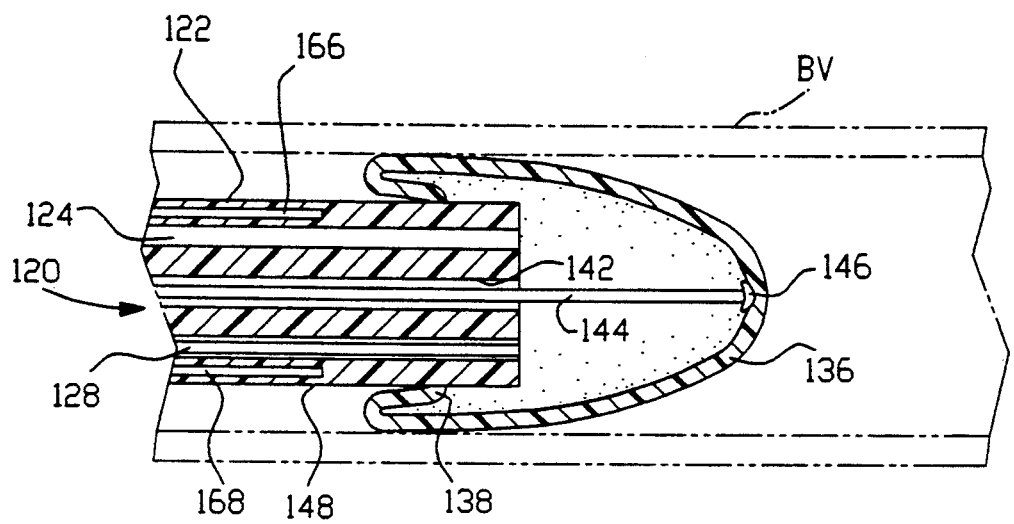
Figure 4C:
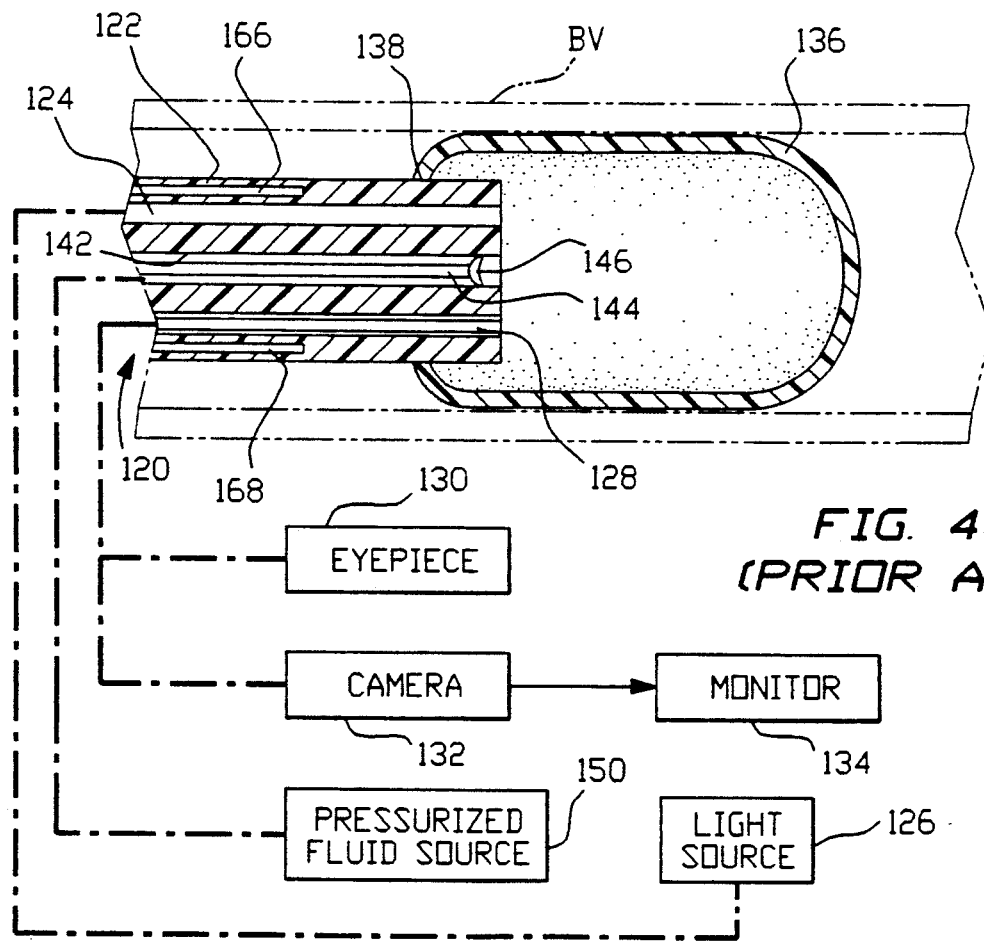

FIGS. 4A–4C illustrate another endoscopic device 120 which may be used in an intussusception reduction procedure in accordance with the present invention. Endoscopic device 120 comprises an elongate flexible endoscopic insertion member 122. An optical fiber 124 extends longitudinally through endoscopic insertion member 122 for guiding visible electromagnetic radiation from a light source 126 (FIG. 4C) to a distal end of the endoscopic insertion member. An image transmission guide in the form of a bundle of optical fibers 128 also extends longitudinally through endoscopic insertion member 122 for transmitting an image from the distal end of the insertion member to an eyepiece 130 at a proximal end of the insertion member. Alternatively, fiber optic bundle 128 may be operatively connected to a camera 132, for example, a charge coupled device ("CCD") which in turn is connected to a video monitor 134 for displaying the image transmitted via fiber optic bundle 128. Various lenses and transparent cover plates have been omitted from the drawings for purposes of clarity.

Endoscopic device 120 further comprises a balloon 136 with a mouth 138 attached about the distal end of insertion member 122 so that a distal tip of the insertion member is disposed inside or enclosed by the balloon. Balloon 136 is made of a material transparent to optical radiation. Accordingly, objects disposed outside of balloon 136 are visible in an image transmitted over fiber optic bundle 128 to eyepiece 130 or camera 132.

Endoscopic insertion member 122 is provided with a biopsy channel 142 in which a flexible rod member 144 is slidably disposed. Rod member 144 is provided at a distal end with a headpiece or flange 146 made of a flexible material.

As illustrated in FIG. 4A, balloon 136 is initially in a collapsed configuration and is flattened back against a cylindrical outer surface 148 of endoscopic insertion member 122 during an insertion of that member in an upstream direction through a colon BV.

Upon a disposition of the distal end of insertion member 122 at a predetermined section of colon BV, rod 144 is pushed in the distal direction to shift balloon 136 out in front of the endoscopic insertion member, as illustrated in FIG. 4B. Simultaneously with or subsequently to the partial ejection of rod 144 from the distal end of endoscopic insertion member 122, a pressurized fluid source 150 (FIG. 4C) is connected to channel 142 to inflate balloon 136. The fluid from source 150 is preferably an optically transparent saline solution appropriate for intravenous feeding.

Balloon 136, as well as other balloons described herein, is effective to displace at least some fecal matter from the distal end of endoscopic insertion member 122 to form a transparent pocket or space, thereby facilitating visual inspection of an intussusscepted intestinal section SIS. Upon an inflation of balloon 136 to a sufficient size, rod 144 may be retracted back into channel 142. As illustrated in FIG. 4C, headpiece or flange 146 deforms to function as a one-way valve, preventing an untimely contraction of balloon 136. To deflate balloon 136, rod is pushed partially out of channel 142.

Instead of inflating balloon 136 via biopsy channel 142, inflation may be accomplished via an auxiliary channel 140 (FIG. 4A) provided in endoscopic insertion member 122.

Tensioning cables 166 and 168 inside endoscopic insertion member 122 are selectively placed under tension to control the direction in which the distal end portion of endoscopic insertion member 122 is turned.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for reducing intussussception, comprising the steps of:
   introducing into a colon a flexible insertion member of an endoscope;
   moving said insertion member through the colon;
   using optical components of said endoscope to view contents and surfaces of the colon during said step of moving;
   upon visualization of a small intestine section folded back into the colon, inflating a balloon at a distal end of said insertion member, said balloon being transparent to optical radiation;
   pushing the inflated balloon against the folded-back small intestine section to force the small intestine section out of the colon; and
   optically monitoring, via said optical components and through said balloon, the folded-back small intestine section and the colon during said step of pushing.

2. The method defined in claim 1 wherein said balloon is attached to an outer surface of said insertion member.

3. The method defined in claim 2 wherein said step of inflating includes the step of forcing a fluid under pressure through an auxiliary channel provided along an outer surface of said insertion member.

4. The method defined in claim 2 wherein said step of pushing comprises in part the step of shifting said insertion member of said endoscope further in a distal direction through the colon.

5. The method defined in claim 2, further comprising the steps of attaching said balloon in a collapsed configuration to said outer surface prior to said step of introducing and removing said balloon from said outer surface subsequently to a withdrawal of said insertion member from the colon after completion of said step of pushing.

6. The method defined in claim 1 wherein said balloon is attached to a distal end of a flexible tube disposed at least partially in a biopsy channel in said insertion member, said balloon being disposed in a collapsed configuration inside a distal end portion of said biopsy channel prior to said step of inflating, further comprising the step of shifting said tube through said biopsy channel to eject said balloon from said distal end portion of said biopsy channel upon visualization of the folded-back small intestine section and prior to said step of inflating.

7. The method defined in claim 6, further comprising the steps of deflating said balloon upon completion of said step of pushing and withdrawing said insertion member from the colon.

8. The method defined in claim 7, further comprising the step of retracting the deflated balloon back into said distal end portion of said biopsy channel prior to said step of withdrawing.

9. The method defined in claim 6 wherein said step of pushing comprises in part the step of shifting said tube further in a distal direction through said biopsy channel.

* * * * *